United States Patent [19]

Temple

[11] Patent Number: 5,312,384
[45] Date of Patent: May 17, 1994

[54] INCONTINENCE DEVICE AND APPLICATOR

[76] Inventor: John E. Temple, 523 Wilkinson, Chelsea, Mich. 48118

[21] Appl. No.: 907,754

[22] Filed: Jun. 29, 1992

Related U.S. Application Data

[63] Continuation-in-part of Ser. No. 778,989, Nov. 7, 1991, which is a continuation-in-part of Ser. No. 98,073, Sep. 18, 1987, Pat. No. 4,850,986.

[51] Int. Cl.$^5$ ............................................. A61F 5/44
[52] U.S. Cl. ................................................... 604/355
[58] Field of Search ............... 604/326, 327, 345, 349, 604/355; 446/69

[56] References Cited

U.S. PATENT DOCUMENTS

| | | | |
|---|---|---|---|
| 2,448,938 | 9/1948 | Wayne | 128/285 |
| 2,548,149 | 4/1951 | Fowler . | |
| 2,564,773 | 8/1951 | Wade . | |
| 3,522,807 | 8/1970 | Millenbach | 128/283 |
| 3,523,534 | 8/1970 | Nolan . | |
| 3,548,828 | 12/1970 | Vasile | 604/328 |
| 3,604,421 | 9/1971 | Pizzella | 604/355 |
| 3,804,093 | 4/1974 | Fell . | |
| 3,938,521 | 2/1976 | Ritota et al. | 604/328 |
| 4,030,500 | 6/1977 | Ronnquist | 604/328 |
| 4,067,335 | 1/1978 | Silvanor | 604/328 |
| 4,117,847 | 10/1978 | Clayton | 604/328 |
| 4,253,460 | 3/1981 | Chen et al. . | |
| 4,269,148 | 5/1981 | Holley-Donawa | 604/355 |
| 4,347,843 | 9/1982 | De Zaepffel | 604/345 |
| 4,368,733 | 1/1983 | Sanidas | 128/283 |
| 4,445,898 | 5/1984 | Jensen | 604/337 |
| 4,496,356 | 1/1985 | Lognion | 604/328 |
| 4,650,817 | 3/1987 | Allen, Jr. et al. | 523/105 |
| 4,784,654 | 11/1988 | Beecher | 604/329 |
| 4,795,449 | 1/1989 | Schneider et al. | 604/326 |
| 4,850,986 | 7/1989 | Temple | 604/332 |
| 5,104,013 | 4/1992 | Hawley | 222/568 X |
| 5,248,071 | 9/1993 | Ray | 222/568 |

FOREIGN PATENT DOCUMENTS

| | | |
|---|---|---|
| 7703562 | 10/1978 | Netherlands . |
| 113453 | 1/1926 | Switzerland . |
| 8701581 | 3/1987 | World Int. Prop. O. .......... 604/328 |

OTHER PUBLICATIONS

"Introducing the Hollister Fecal Incontinence Collector," brochure, 7 pp., by Hollister, Inc.

Primary Examiner—Randall L. Green
Assistant Examiner—Mary B. Jones
Attorney, Agent, or Firm—Krass & Young

[57] ABSTRACT

An incontinence device and applicator therefor. The incontinence device comprises a generally tubular, soft latex bag which tapers to an opening at an upper end thereof. An area adjacent said opening is adapted to be adhesively attached to the tissue overlying the anal sphincter of a patient. The applicator is adapted to fit within the incontinence device. It includes an elongated handle and a head attached thereto, the head being configured to fit against the anal area of the user and bring the attachment of the device to bear against the anal tissue for adhesive attachment thereto. The head includes an oval, ring-shaped bearing surface and means for adjusting the size of the bearing surface so that the device may be used on patients displaying a wide range of anatomical variation. A method of making the incontinence device by vacuum molding is also disclosed.

7 Claims, 9 Drawing Sheets

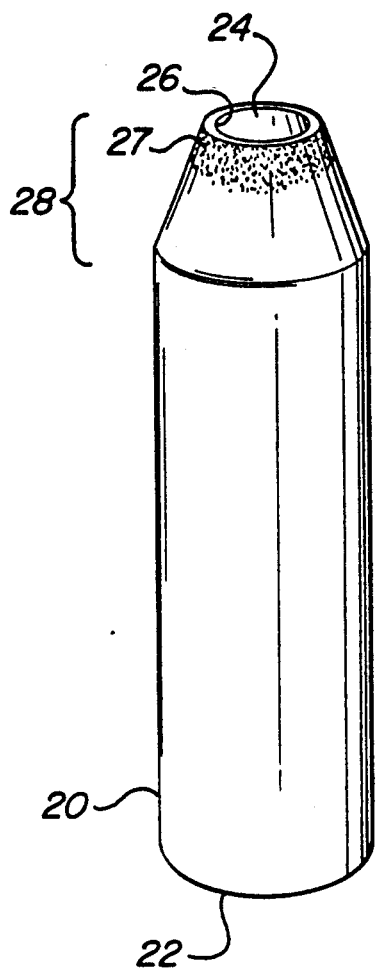
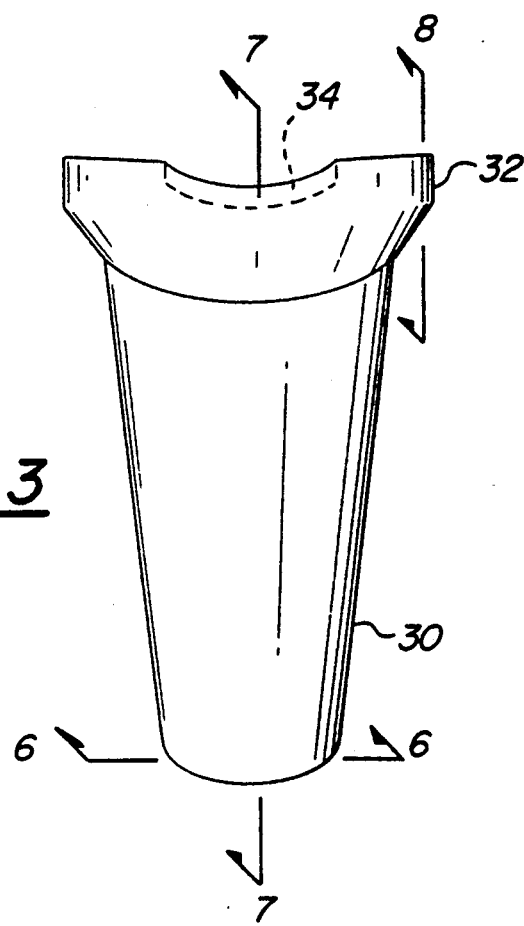
FIG-1
FIG-3

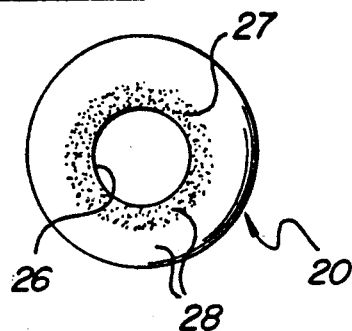
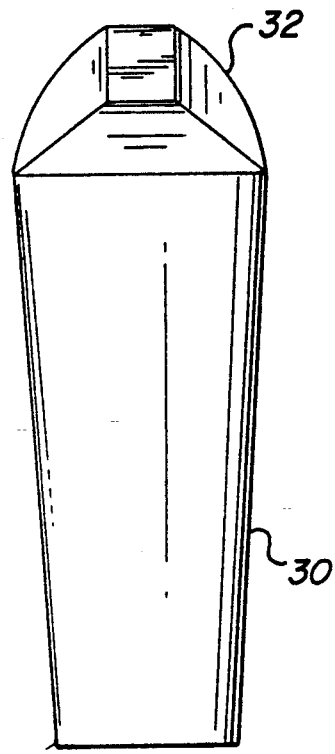
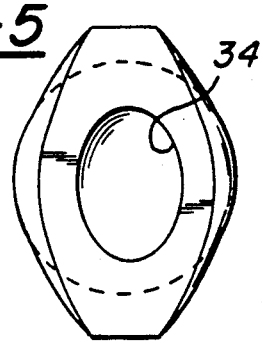
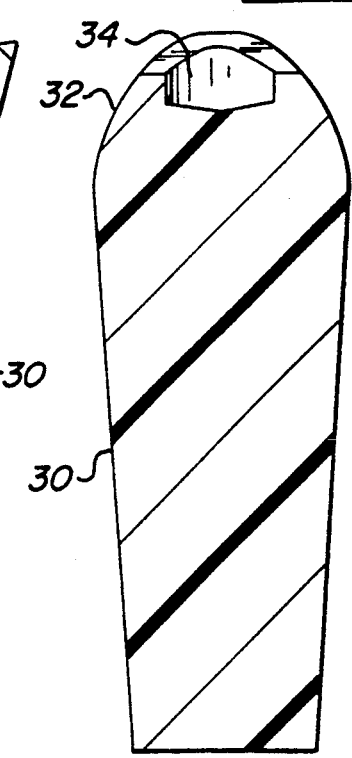

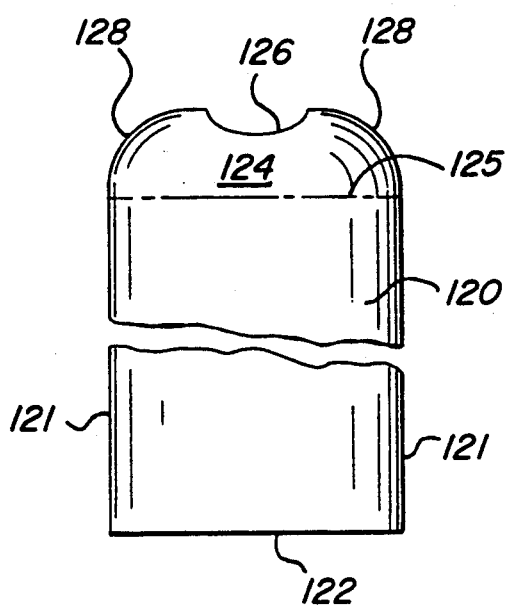
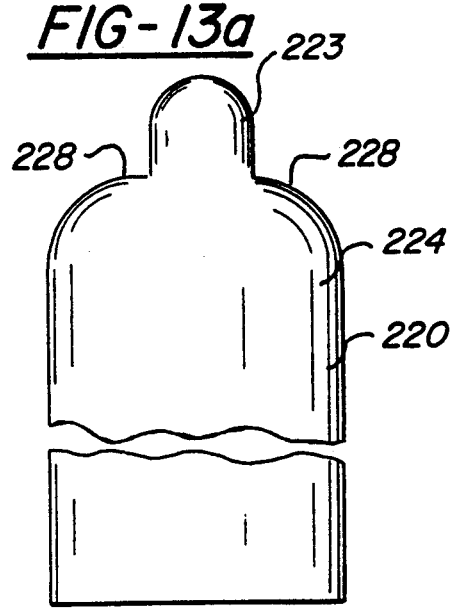
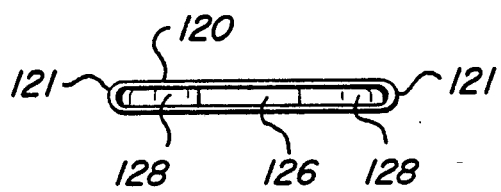
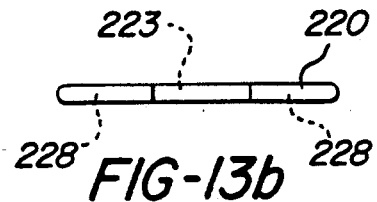
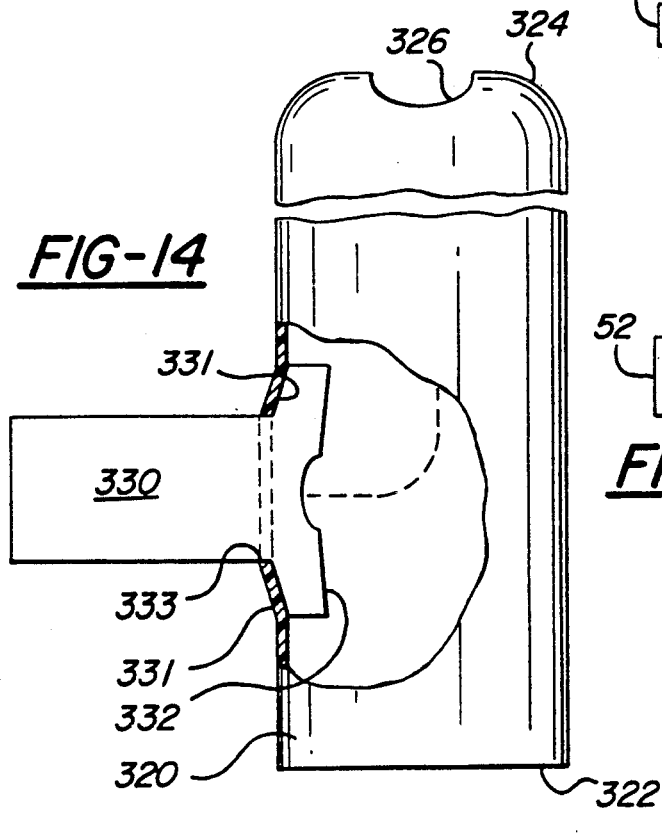
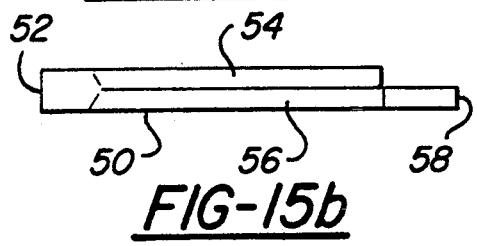
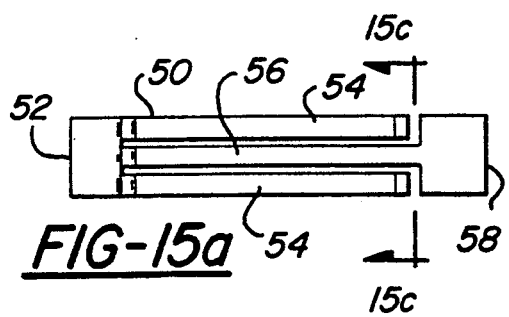
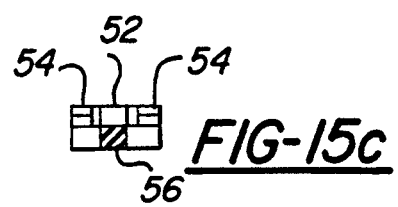

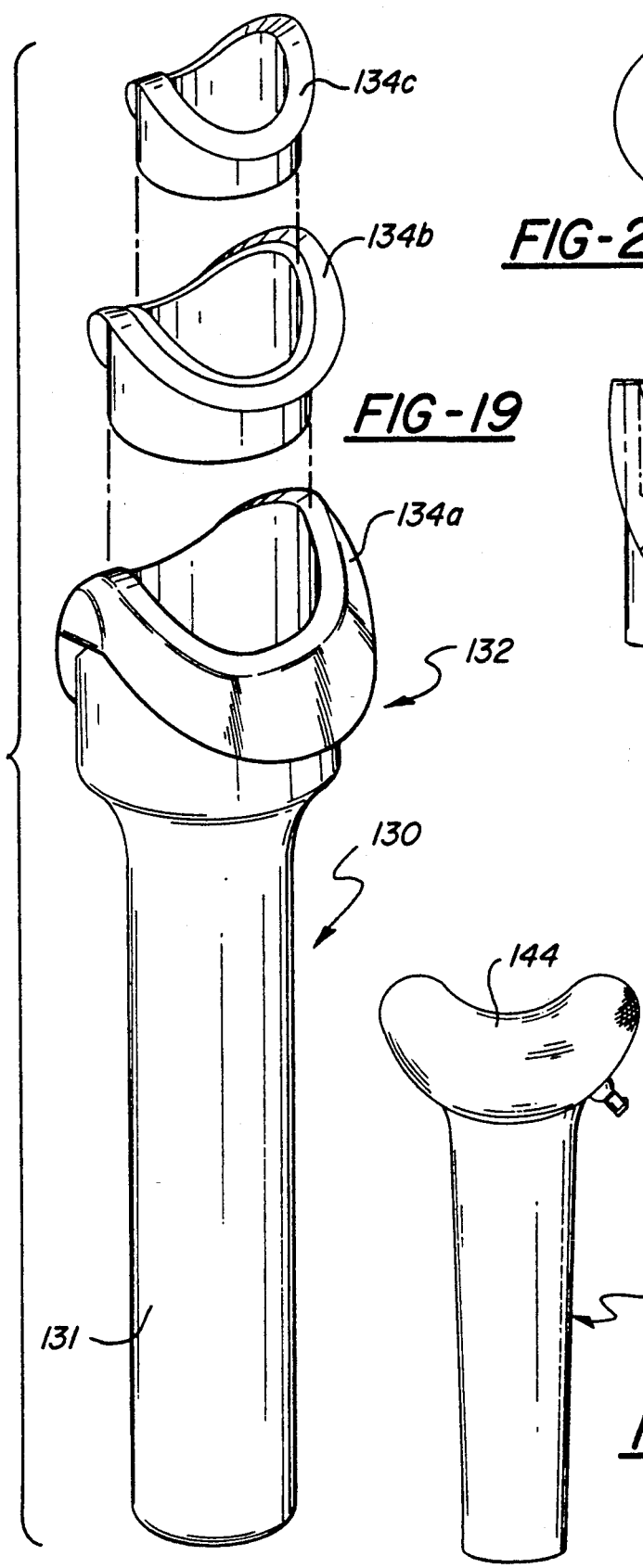

INCONTINENCE DEVICE AND APPLICATOR

REFERENCE TO RELATED APPLICATIONS

This application is a continuation-in-part of Ser. No. 778,989, filed Nov. 7, 1991, which is the U.S. National Phase of PCT/US89/01960 filed May 8, 1989, which in turn is a continuation-in-art of U.S. application Ser. No. 07/098,073, filed Sep. 18, 1987, now U.S. Pat. No. 4,850,986.

BACKGROUND OF THE INVENTION

The field of the invention pertains to medical appliances and, in particular, to devices that can be attached to the exterior skin of a person about or in an opening with the purpose of accepting and containing any solid or liquid material flowing from the opening. Such devices require a means of attachment that does not damage the skin but is reasonably secure.

Lognion, U.S. Pat. No. 4,496,356, discloses an anal excretion collection rectal catheter that is insertable beneath the sphincter muscles about the opening. The Lognion device comprises a collecting tube open at one end with a resilient ring that fits within the rectal opening.

Wade, U.S. Pat. No. 2,564,773, discloses a therapeutic agent comprising a thimble and latex bag insertable into a bodily opening for the collection of fluids. The bag folds within the thimble before use and may be attached to the thimble with an adhesive. The thimble includes an opening for the admission of fluids and is directly insertable into the bodily opening.

Wayne, U.S. Pat. No. 2,448,938 and Swiss Patent No. 113 453 each disclose a sanitary protective appliance of similar structure to receive bodily fluids and semi-solids from infections and incisions. The appliances comprise soft thin rubber tubes of accordion like shape with an opening of relatively large diameter. On the inside surface adjacent the opening is an adhesive ring to enable the device to be adhesively attached to the skin about the body opening from which there is a discharge.

Chen et al., U.S. Pat. No. 4,253,460 and Allen, Jr. et al., U.S. Pat. No. 4,650,817 both disclose adhesives suitable for attaching appliances such as ostomy devices to the skin about a body opening. Such adhesives must be secure, reasonably fluid tight but nevertheless easy to remove without damage to the skin.

U.S. Pat. No. 3,522,807 discloses an incontinence bag that has a pleated arrangement about the anus to expand and contract with the opening and closing of the anus. The overlapping leaves of the pleats do not provide for complete adhesive attachment to the skin thus permitting leakage and providing a difficult attachment.

U.S. Pat. No. 4,445,898 discloses a foam backed skin barrier attachment and incontinence bag. The skin barrier is disclosed as soft, pliable, stretchable and contractible foam backed plastic 0.080 to 0.400 inches thick. Plastic backed by foam has limited stretchability of less than 25% which limits the expandability of the anal hole in the skin barrier to an amount less than needed for most patients. In such cases, the anus can not open sufficiently, thereby causing severe pain, or the adhesive fails and the bag detaches and leaks.

Devices insertable within body openings have been found to cause permanent damage to the sphincter muscles after prolonged use. With a view toward overcoming and avoiding damage to the sphincter muscles of the anal opening but nevertheless providing a secure receptacle for bodily waste that does not damage the skin surrounding the anus, is sufficiently elastic (an elastic limit of about 200% or more) to accommodate the full opening of the anus and is easy to install, the herein named inventor developed the incontinence devices and applicators disclosed in U.S. Pat. No. 4,850,986 and PCT/US89/019601.

The devices disclosed therein have proven to overcome the disadvantages of the prior art noted above in that they provide an incontinence bag for holding body fluids which may be securably attached to, for example, the anus of a fecally incontinent person by means of the applicator disclosed therein. The bag remains securely attached during use, and attachment and removal are relatively simple. However, many fecally incontinent persons have hemorrhoids or other pathological conditions which limit the usefulness of the incontinence device. It is too uncomfortable to the user to adhere anything to hemorrhoidal tissue, which is unusually sensitive. Therefore, a bag with a larger hole must be used so that the bag may be attached to the tissue around the hemorrhoidal tissue. However, my previously disclosed applicators are primarily used to attach a bag having a standard size hole directly onto the skin overlying the anal sphincter.

SUMMARY OF THE INVENTION

The incontinence device comprises a generally tubular soft latex shape, tube or bag open at both ends but having a clip to retain the lower end partially folded up and closed. The upper end of the device is curved and tapered inward to the opening with the latex minimal thickness, preferably 0.003 to 0.006 inches (0.076 to 0.152 millimeters), and coated on the outside with a suitable adhesive for contact with the skin about the anal opening. The latex is purposefully made as thin as possible to enable the latex to offer little or no resistance to stretching with the skin as the anus is fully opening and closed by the sphincter muscles. Soft latex of the above thickness has a better than 400% elastic limit.

A specifically shaped applicator is provided to enable a nurse or physician to easily apply the adhesive to the device and to conveniently and securely attach the adhesive and latex about the upper opening to the skin about the anus. The applicator fits within the tube and is removed through the lower end of the tube. The clipped lower end also permits the tube to be periodically opened to permit gases accumulated therein to be expelled, or fecal matter to be removed and the bag to remain on the patient.

In an alternate version of the device, the device is formed of latex or an extended polyvinyl chloride/urethane mixture of similar elastic limit. The device is initially manufactured as a substantially flat hollow tube. Because of the extreme thinness of the device wall thickness, the hollow tube can expand into a substantially round tube as needed.

The applicator in alternative embodiments may be permanently attached to the device and also serve as a vent for liquids. In this construction the applicator is permanently mounted in the sidewall of the device and may or may not penetrate the wall. If the liquid vent is included then the applicator is located near the bottom of the device and penetrates the wall. Gases and liquids can be vented and when the device is filled with fecal matter it can be disposed conveniently. Such a combination simplifies the use of the device and eliminates the possibility of a non-sterile or contaminated applicator being improperly reused.

In another preferred embodiment of the applicator and device of the present invention, the applicator includes an elongated handle and a head attached thereto, the head including an oval, ring shaped bearing surface for bearing against the tissue surrounding a bodily orifice of a patient so that an incontinence device may be adhered to the tissue. Means are provided for adjusting the size of the bearing surface such that the incontinence device may be adopted for use on patients displaying a wide range of anatomical variation. For example, a patient may have hemorrhoidal tissue or other pathology present in the anal region. It would be to uncomfortable for the patient to attach the fecal incontinence bag directly to the hemorrhoidal tissue surrounding the anal sphincter. It would be more desirable to attach the device to the skin surrounding the hemorrhoidal tissue. Of course, the opening in the incontinence device would have to be larger to accommodate and surround the hemorrhoidal tissue. In such a situation, an applicator which provides only a fixed size bearing surface for attaching the device to the tissue may not be suitable. By providing the head of the bearing surface with means for adjusting the size of the bearing surface, the applicator and incontinence device may be used with a wider variety of patients.

In one embodiment of the adjustable bearing surface applicator, the means for adjusting the bearing surface comprise a plurality of concentric rings, each including a tubular stem and tapering application surface, which rings are disposed in nesting fashion within each other. At least the smallest of these concentric rings, which are snap fit into each other may be removed so as to vary the size of the bearing surface. Alternatively, an inflatable, elastic ring may be provided which, when injected with fluid, inflates to vary the size of the bearing surface.

A method of manufacturing an incontinence device by vacuum molding and subsequent edge-sealing is also disclosed.

DESCRIPTION OF THE DRAWINGS

FIG. 1 is a perspective view of the device;

FIG. 2 is an upper end view of the device;

FIG. 3 is a perspective view of the applicator;

FIG. 4 is an end view of the applicator;

FIG. 5 is a top view of the applicator;

FIG. 6 is a cross section of the applicator taken along the line 6—6 of FIG. 5;

FIG. 7 is a cross section of the applicator taken along the line 7—7 of FIG. 5;

FIG. 8 is a cross section of the applicator taken along the line 8—8 of FIG. 5;

FIGS. 12a and 12b illustrate in side and bottom view an alternate flat form of the device;

FIGS. 13a and 13b illustrate in side and bottom view a dipping tool to make the alternate flat form of FIG. 12;

FIG. 14 is a cutaway side view of the device having the applicator permanently attached;

FIGS. 15a, 15b and 15c illustrate a closure clamp for the device in plan view, side view and end view respectively;

FIG. 19 is a perspective view of an applicator according to the present invention having an adjustable bearing surface;

FIG. 20 is an end view of the applicator of FIG. 19 showing the concentric rings nested therein;

FIG. 21 is a side view of the applicator of FIG. 19 showing the concentric rings nested therein;

FIG. 22 is a cross-sectional view of the applicator of FIG. 20 taken along lines 22—22;

FIG. 23 is another embodiment of the adjustable bearing surface applicator of the present invention.

DESCRIPTION OF THE PREFERRED EMBODIMENTS

Figure 9:
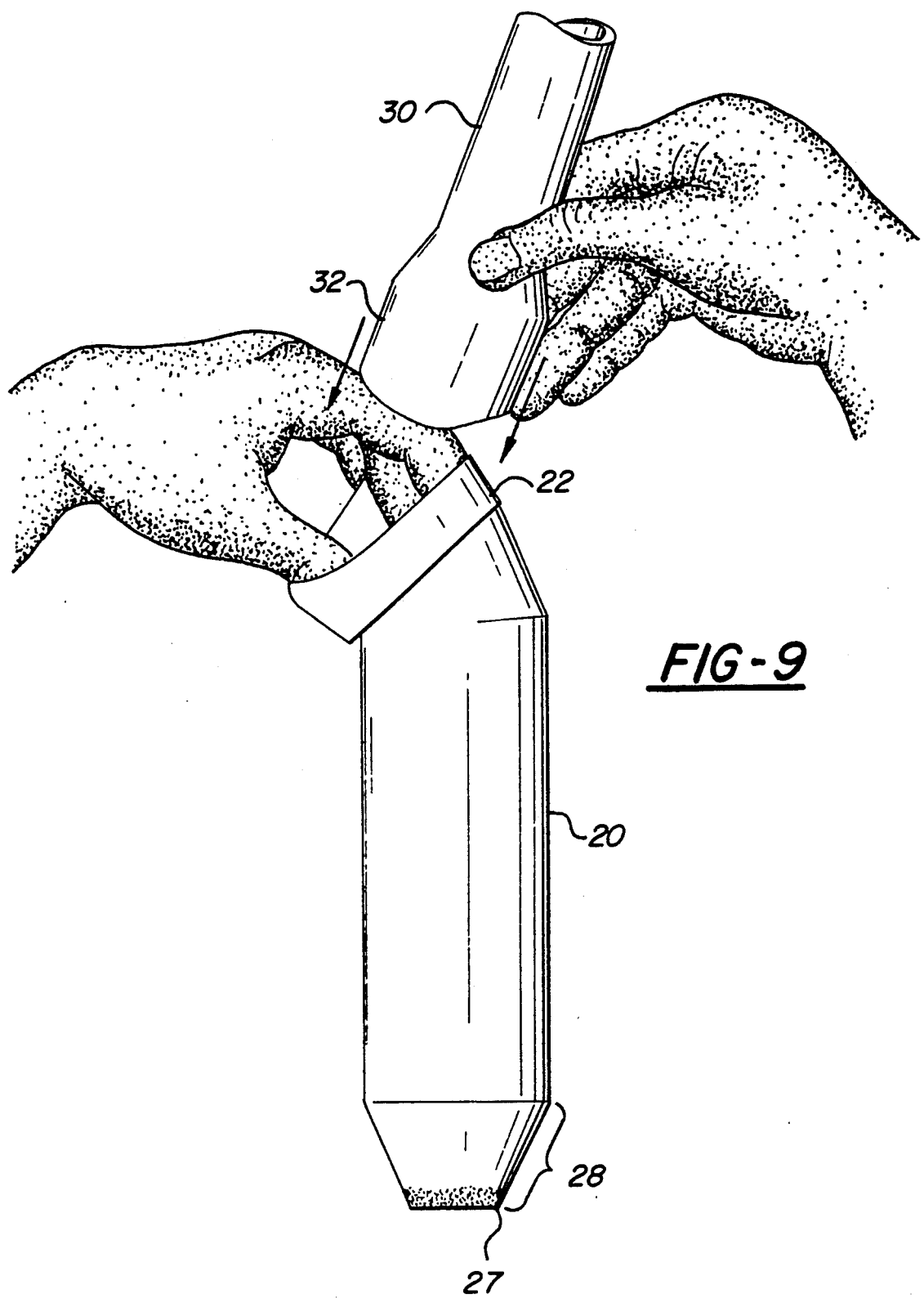
FIG. 9 illustrates insertion of the applicator into the device.

Illustrated in FIGS. 1 and 2 is a generally tubular shape 20 formed of soft latex, polyvinyl chloride/urethane, or a similar material that is liquid impermeable, very flexible and soft to the skin. The lower end 22 is open. As illustrated below the lower end may be closed by folding over and retaining with a plastic closure clip (not shown). The device is suitably about 18 inches long and 3 inches in diameter. With the exception of the upper end 24 a wall thickness of about 0.010 to 0.0020 inches (0.254 to 0.051 millimeters) is suitable.

The upper end 24 includes an opening 26 of about one and one-quarter inches in diameter surrounded by an upper curved generally conical portion 28 extending down to the tubular shape 20. The curved upper portion 28 is made specifically very thin for maximum elasticity and flexibility and adjacent the opening 26 is coated on the outside 27 just prior to use with an adhesive suitable for secure attachment to the skin.

Since the human skin about the anal opening stretches and contracts a substantial amount with opening and closing of the anal sphincter muscles, the conical portion 28 must also stretch and contract with minimal resistance and maximum flexibility to prevent chafing of the skin and failure of the adhesive attachment. A thickness of 0.003 to 0.006 inches (0.076 to 0.152 millimeters) for soft latex has been found preferable with a two part adhesive comprising polyolmethylsiloxane in trichlorotrifluoroethane. Thicknesses of about 0.015 inches (0.381 millimeters) for the latex adjacent the upper opening have been found too inflexible for satisfactory use although a thickness of less than 0.010 inches (0.254 millimeters) is serviceable. The thinned latex has been found far superior to most film plastics by providing elasticity on the order of 400%, or more. Latex of 0.001 inches (0.0254 millimeters) provides additional flexibility, however, the minimal thickness is more difficult to manufacture. A plastic material recently available (KRATON TM, Shell Chemical Company, Houston, Tex., U.S.A.) at thicknesses similar to the latex or less has adequate elongation (400%) an appears to be a possible option but requires greater force to provide the elongation.

It has also been found that a polyvinyl polyurethane mixture of a suitable thickness may also be used to fabricate the device of the present invention. Preferably, a thickness of 0.001 to 0.004 inches is used, thereby resulting in a device having an elongation of approximately 200 percent. One advantage to using a polyurethane bag is that odor problems sometimes encountered with latex bags are largely eliminated. Due to its more porous nature, fecal odors can sometimes "bleed" through a latex device, a particularly undesirable result if the patient wearing the device is suffering from gastro-intestinal bleeding. Urethane is less porous, and little or no odor problem occurs, even with GI bleeders.

The inside of the device is preferably coated with a suitable lubricating powder to prevent the sticking of stools to the inside of the latex tube.

Illustrated in FIGS. 3 through 8 is an applicator comprising a handle portion and shaped top 32. As shown the top 32 is generally saddle shaped with a depressed oval center 34. The saddle shape 32 is specifically to fit the skin and muscle structure about the human male or female anus. The saddle shape 32 is sized to fit within the conical portion 28 of the device. More particularly, the conical portion 28 is stretched over the applicator saddle shape 32 after insertion of the applicator from the open lower end 22 as shown in FIG. 9.

Figure 10:
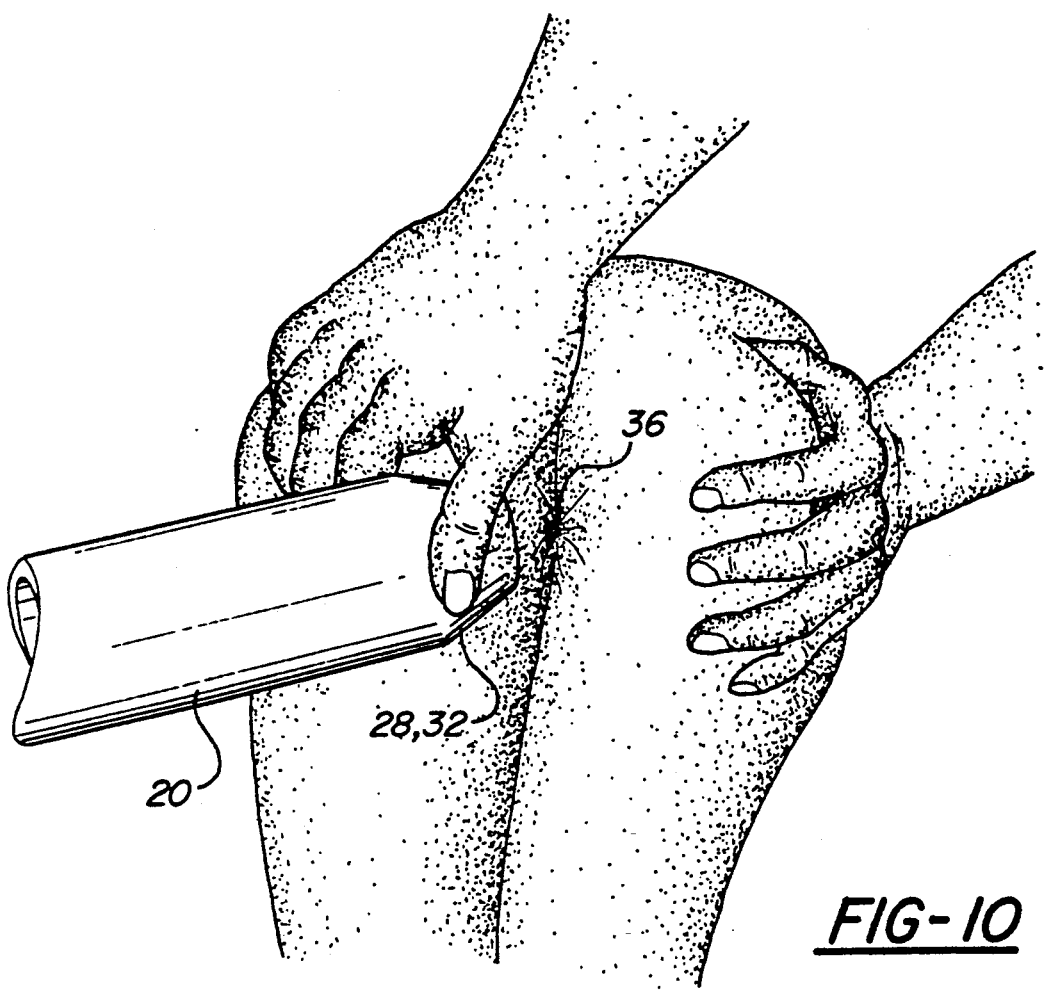
FIG. 10 illustrates attachment of the device.
Figure 11:
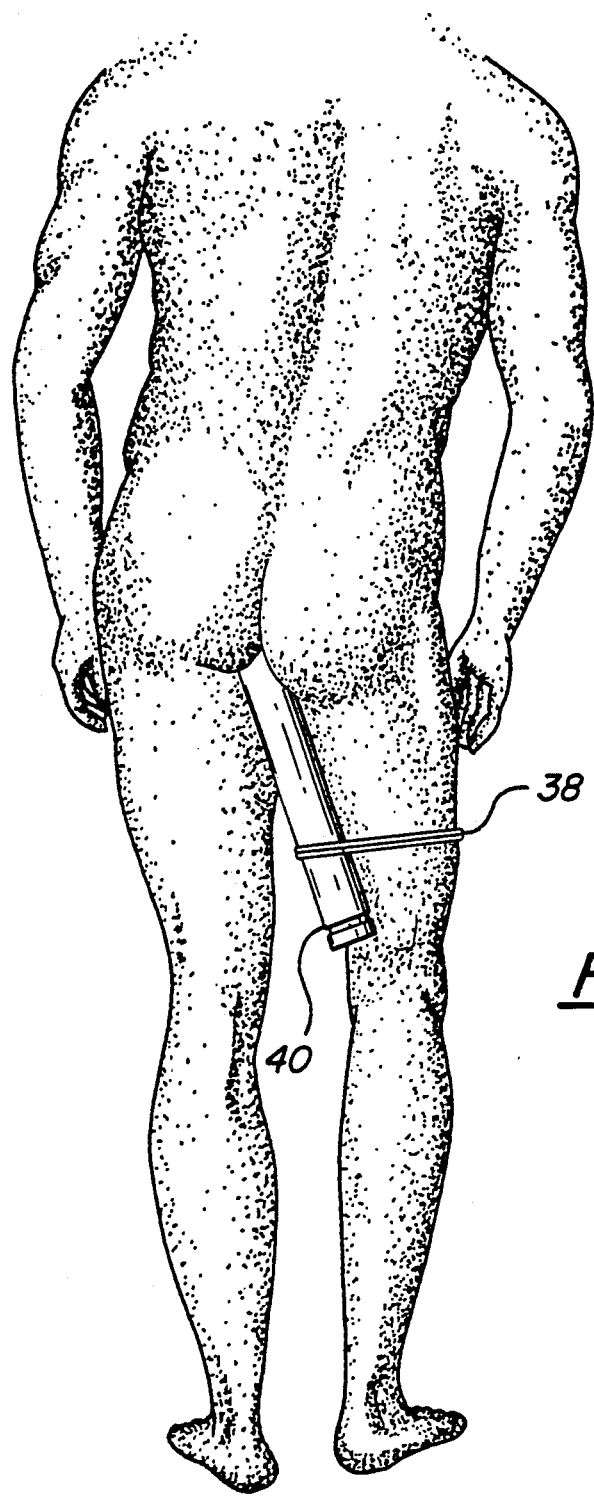
FIG. 11 illustrates the device in place.

As best shown in FIG. 10, the device 20 with the applicator held thereinside and the conical portion 28 stretched smoothly over the saddle shape is spray coated with adhesive and applied about the anus 36. In place as shown in FIG. 11 the device may be lightly taped at 38 to the thigh and folded and clipped at 40.

In FIGS. 12a and 12b an alternate form of the incontinence device is illustrated in its manufactured shape. Whereas the first embodiment shown in FIG. 1 is manufactured on a substantially cylindrical mandrel tapered toward the top, the alternate form of FIGS. 12a and 12b is formed flat as further described below.

As shown in FIGS. 12a and 12b the device comprises a hollow flat tube 120 constructed of soft latex or a plastic having the required elasticity or elongation such as a recently developed composite of extended polyvinyl chloride/urethane (polyurethane). The bottom end 122 of the tube 120 is open. The upper end 124 is edgewise curvedly tapered 128 toward an opening 126 into the interior of the device.

The material thickness over the curvedly tapered portion 128 must be sufficiently thin to provide the flexibility, elasticity and elongation sufficient to substantially equal or exceed that of the human skin over the anus. A suitable thickness range is 0.0015 to 0.0045 inches (0.0381 to 0.0114 millimeters) for the curvedly tapered portion 128 over the entire upper end 124 (above the ghosted line 125) on both sides. The major portion of the device below the line 125 may be thicker as desired and preferably is about 0.003 to 0.020 inches (0.076 to 0.508 millimeters) in thickness.

Illustrated in FIGS. 13a and 13b is a mandrel or dipping tool to form the incontinence device or bag of FIGS. 12a and 12b. A suitable material is buffed aluminum plate ½ inches (about 12 millimeters) in thickness and formed with a straight portion 220 and curvedly tapered portion 228 at the upper end 224. A tongue 223 extends from the upper end 224 from which the mandrel can be suspended for dipping into the latex bath.

The mandrel is lowered into the bath and then slowly withdrawn. The thickness of the latex is determined by the time in the bath; therefore, the mandrel is first relatively quickly and evenly partially withdrawn upon creation of the exceptionally thin upper end 124 of the incontinence device or bag. The mandrel is then subsequently fully withdrawn upon formation of the thicker body 120 of the device.

After drying, curing and stripping from the mandrel, the opening 126 in the upper end 124 is die cut through the upper end as the device lies flat.

Figure 24:
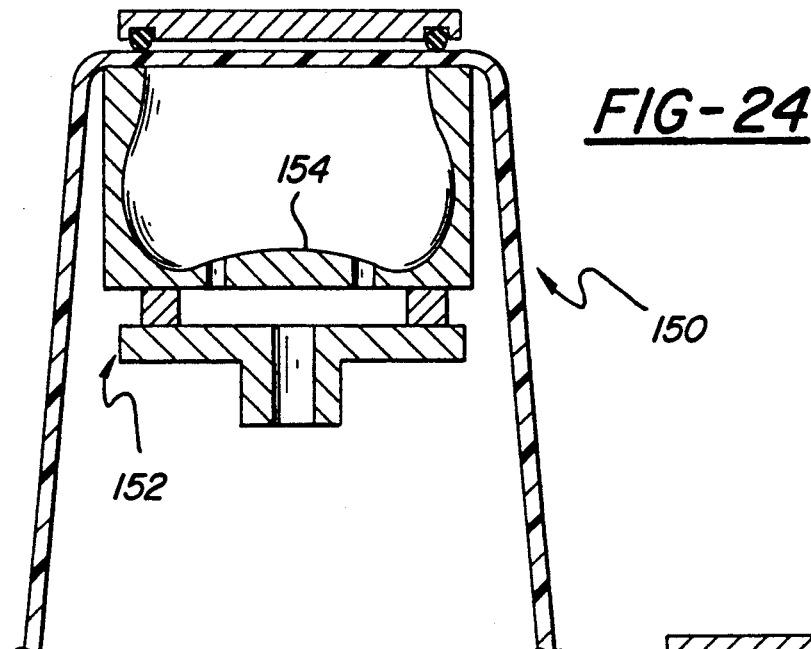
FIGS. 24 and 25 illustrate two steps of a vacuum molding process used in manufacturing a device according to the present invention.
Figure 25:
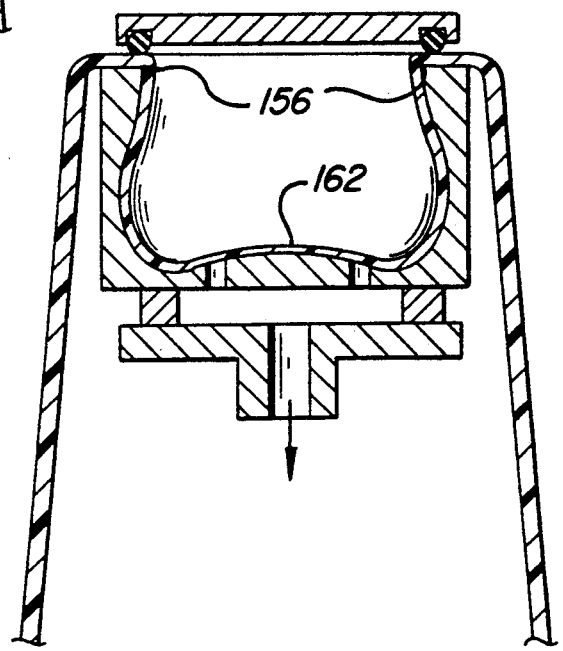
Figure 26:
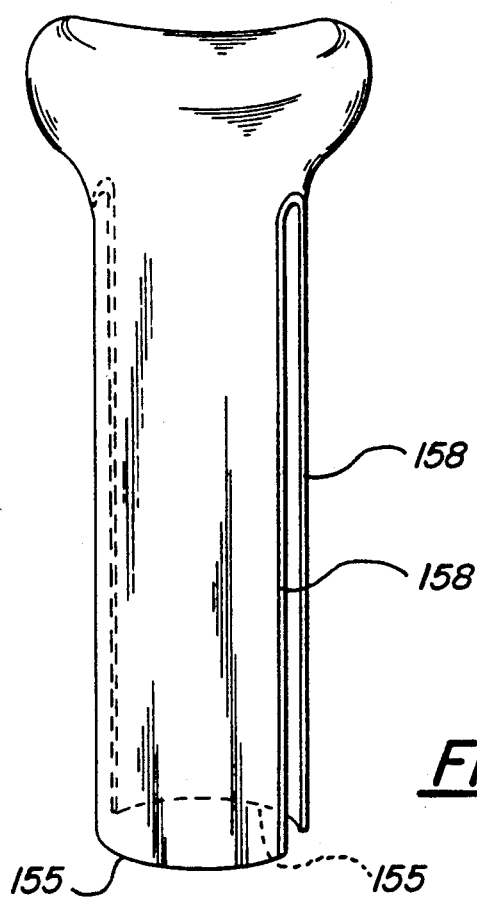
FIG. 26 shows the device at another stage of manufacture.

An alternate method for manufacturing the incontinence device of the present invention is illustrated in FIGS. 24-26. This method involves the use of a negative vacuum molding operation to form the tapering end of the incontinence device. A heated plastic sheet 150, preferably formed of polyurethane, is laid over a concave mold 152 with a saddle shaped mold cavity 154. Optionally, the preheated plastic sheet 150 is subjected to further heating during the molding process. The sheet 150 includes a pair of opposed end edges 155 and opposed side edges 158 which extend beyond the mold cavity 154 when the sheet 150 is laid thereover, in the manner depicted in FIG. 24. Air is then evacuated from the mold 152 in the direction shown by the arrow in FIG. 25, thus drawing the sheet 150 by suction into the mold cavity 154. Since the mold cavity 154 has an opening 156 of larger diameter, the portion of the sheet 150 forced into the mold cavity 156 will be molded in a saddle shape matching the saddle shape of the applicator.

As can be seen from FIG. 25, the saddle shaped, molded portion of sheet 150 will be thinner than the unmolded portions of the sheet. This thickness can be varied by the depth of the draw and the thickness of the initial material. Therefore, the desired thickness of the molded attachment portion of 0.001 to 0.004 inches can be obtained from much thicker stock material, i.e., 0.006 to 0.025 inches. As explained above, it is important for the practice of the present invention that those portions of the device surrounding the anal area of a patient be particularly elastic to accommodate movements of the anal sphincter. A device manufactured in accord with the present invention will have a particularly elastic area surrounding the anus because this is the portion which is forced into the vacuum mold cavity during the molding process.

After molding, the sheet 150 is allowed to cool and removed from the mold 152. The opposed end edges 156 are then brought into alignment with each other, as can be seen in FIG. 26. This has the effect of folding each side edge 158 onto itself. Each folded side edge 15 is then sealed to produce a closed bag. A suitably sized opening (for surrounding the anal region) is then formed in end wall 162, and the side and end edges 158,156 are then trimmed as desired, or the opening can be cut during the drawing process by using a simple punch.

Illustrated in FIG. 14 is a modified incontinence device wherein the handle 330 of the applicator extends through the tubular wall 320 of the device. The saddle shaped top 332 of the applicator is located within the tubular wall 320 and the wall adhesively attached to the underside 331 of the top 332. Thus, the aperture 333 in the wall 320 for the applicator handle 330 is sealed to prevent leakage. With this embodiment the applicator head 332 is permanently inside the device and the upper end 324 can be stretched over the head 332 as in the embodiments disclosed above. However, with this embodiment the applicator is disposable with the device thereby eliminating the likelihood of reuse and contamination from reuse. As a further alternative the entire applicator may be adhesively attached within the device and either grasped through the open lower end 322 or by grasping the device about the handle.

In these embodiments of FIG. 14 the applicator should be located in the lower one-third of the device for reasons of comfort to the patient and so as not to impede the movement of solid fecal matter into the device.

Illustrated in FIGS. 15a, 15b and 15c is a clip for reasonably sealing the lower end of the incontinence devices described above. The clip comprises a three pronged body 50 having a common end 52, two substantially identical side prongs 54 and a central prong 56. As shown the central prong 56 is displaced vertically from the side prongs 54 and includes grasping means 58 similar to the common end 52 which also serves as a grasping means.

To use, the clip is slid over the lower end of the device after the lower end is flattened. The central prong 56 is to one side and the side prongs 54 are to the other side. The clip may then be rolled up several turns and taped.

Figure 16A:
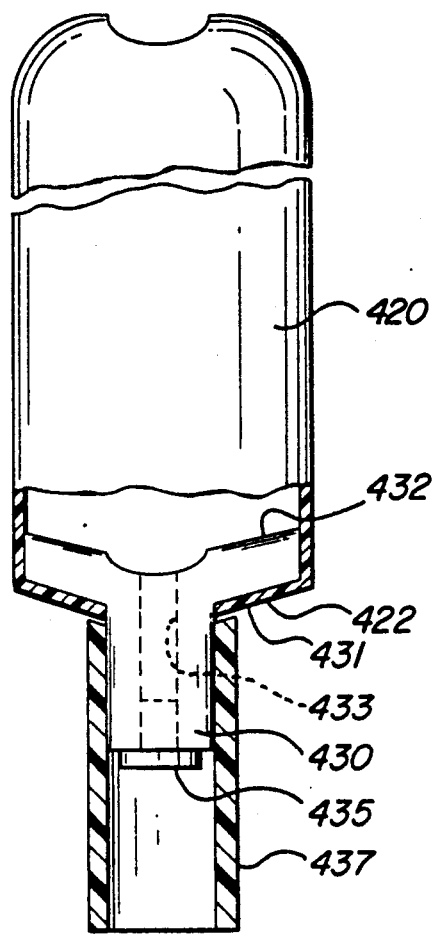
FIGS. 16a and 16b are cutaway side and edge views of the device having the applicator permanently attached at the lower end and fitted with a drainage vent.
Figure 16B:
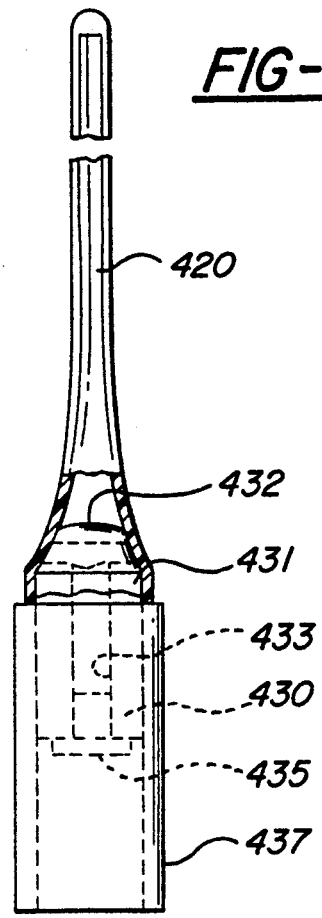

Illustrated in FIG. 16 is a further modification of the device or bag wherein the applicator head 432 is located within the lower end 422 of the device. The handle 430 of the applicator extends below the device and the underside 431 of the applicator is adhesively attached to the device about the lower end 422 to seal the lower end. The handle 430 with extension 437 and head 432 are pierced by a drain hole 433 fitted with a removable cap 435 for release of gases and liquids. This version of the device and applicator obviates the need for clipping or sealing the lower end of the bag and requires the applicator be disposed with the bag.

Figure 17:
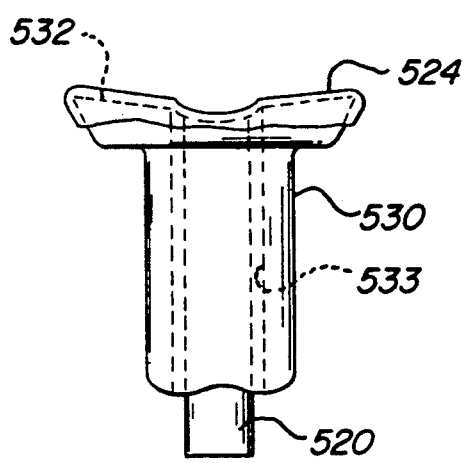
FIG. 17 illustrates an applicator with a central aperture through which extends the device.

The devices illustrated above, whether formed in the substantially round tubular form shown in FIG. 1 or the substantially flat tubular form shown in FIG. 12, can easily be stretched over the saddle shaped application head shown in FIG. 3. Or either form of the device can be manufactured with the saddle shaped applicator therein as shown in FIGS. 14 and 16. The versatility arises from the extreme flexibility and elongation of the very thin latex or plastic material of the device. Or, the device can be threaded through an aperture 533 in the applicator handle 530 shown in FIG. 17. As above the upper end 524 of the device 520 is stretched over the upper end 532 of the applicator. In this embodiment, the upper end of the device may be turned back upon itself before threading through the aperture 533, particularly if the molded upper end has the reduced thickness produced by vacuum molding.

Figure 18A:
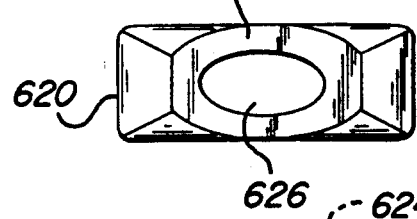
FIGS. 18a and 18b illustrate a device molded to fit the applicator with minimal stretching.
Figure 18B:
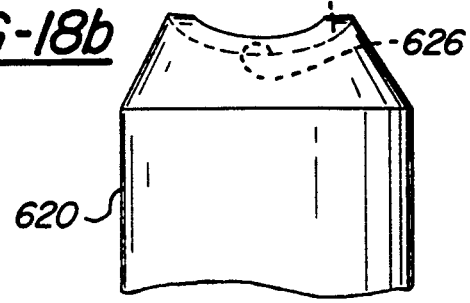

The device may alternatively be constructed of two thin flat sheets of latex or plastic solvent bonded or adhesively adhered along two edges 121 in FIGS. 12a and 12b to form a tube and across one end to form the upper end 128. The upper opening 126 is then cut as above in the final step of manufacturing the dipped form of the device. Or, the device 620 may be mandrel or injection molded to the shape illustrated in FIGS. 18a and 18b wherein the upper end 624 is shaped to conform with the applicator top with minimal stretching and the hole 626 formed in the depression.

The applicator may be made of a variety of materials both hard and flexible. A hard plastic or metal applicator forces the patient's rectal area to take the shape of the applicator. A softer applicator allows the rectal area and applicator to have some deformation. The preferably construction is a soft rubber, silicone rubber or closed cell dense foam that skins over in manufacture to provide a smooth surface. The material chosen is preferably about 55 Durometer and may be attached as a layer on the head of a harder plastic applicator. Or the entire applicator may be formed of an air filled polyvinyl chloride foam that skins over to provide a smooth resilient surface. A new plastic on the marked (SANTOPRENE TM, Monsanto Corporation, St. Louis, Mo., U.S.A.) simulates many characteristics of natural rubber in feel and Durometer. A further advantage is the thermoplastic character permitting easier processing and scrap recycling. Other suitable materials are air filled polyvinyl chloride foam, PVC, polypropylene, etc.

One embodiment of an applicator of the present invention having an adjustable bearing surface is illustrated in FIGS. 19-22. FIG. 19 shows such an applicator 130 having an elongated handle 131 attached to an applicator head 132. Applicator head 132 is comprised of three concentric, oval rings 134a, 134b, 134c. The construction of each concentric ring is best shown in cross section FIG. 22, which shows the nesting arrangement of the rings. Concentric ring 134a is nested inside of and on top of adjoining and radially outwardly disposed concentric ring 134b, which, in turn, nests inside and on top of outwardly radially disposed adjoining concentric ring 134a. Each of the concentric includes a hollow, tubular stem 136 and an outwardly extending lip 137 radially formed on an end of stem 136. Each lip 137 is, in turn, formed of three sections, namely upper surface 138, conically tapering application surface 139 depending from upper surface 138, and lower surface 140 depending from tapering surface 139. It will be noted that the innermost concentric ring 134c is not actually shown with a separate upper surface 138, this being incorporated into tapering surface 139.

In each case, the lower surface 140 of the lip 137 of each concentric ring rests on top of the upper surface 138 of its nearest radially outwardly disposed neighbor. That is, the lower surface 138 of the innermost ring 134c rests upon the lower surface 140 of the middle ring 134b, and so on. In this fashion, the concentric rings are nestably and stackably disposed. A bearing surface of the applicator head 132 is formed by the tapering surfaces 139 of the uppermost of the concentric rings 134a, 134b, 134c. That is, if all three rings are present, the bearing surface will be primarily formed by the tapering surface 139 of innermost ring 134c. If innermost ring 134c is removed, the bearing surface will be formed by the tapering surface 139 of the middle concentric ring 134b. If both inner rings are removed, as is shown in FIG. 19, the bearing surface will be formed by the tapering surface 139 of the outermost ring 134a. The bearing surface of the innermost ring 134c has a smaller central opening, and a smaller outer diameter than the bearing surfaces of the other two rings. Conversely, the bearing surface of the outermost ring 134a has the largest internal and external diameters. Hence, depending on what rings have been removed, the applicator head 132 may have a variety of differently sized and shaped bearing surfaces.

The head 132 of the applicator is, typically, configured so as to be saddle shaped, as can most clearly be seen in FIG. 21, so that the applicator head 132 will conform to the anatomy of a patient who is to wear the incontinence device of the present invention. On a typical patient, the incontinence device will be applied directly to the skin covering the anal sphincter and all rings 134a, 134b, 134c will be nested to form the applicator head 132. However, if the patient has hemorrhoidal tissue or other pathology of the anal region, it will be desirable to remove one or more of the inner rings depending on the particular configuration of the patient's anatomy. The rings are constructed of a soft, resilient material having a smooth surface so that they can be snap fitted into each other by means of a detent (not shown). In this way, one or more inner rings may easily be removed from the applicator head 132 as desired. After the applicator 130 has been configured to fit the particular patient, the device may be used as described above to attach the area 27 adjacent the opening 26 of the incontinence device 20 to the anal area tissue of the patient.

An alternative version of an adjustable applicator of the present invention is shown in FIG. 23. In this version, the applicator 142 is equipped with a hollow, resilient ring 144 which may be inflated with a fluid to expand its volume and increase its surface area. By filling the ring 144 with a suitable amount of fluid, its size may be adjusted to accommodate patients with hemorrhoids or other anal pathologies.

The device and applicator of the present invention have been described with reference to certain exemplifications and embodiments thereof. Doubtless, other design variations may occur to one skilled in the art by employing the teachings of the present invention without departing from the scope thereof. The exemplifications and embodiments described and illustrated are not meant to be limitations on the scope of the present invention which is defined solely by the claims appended hereto and all equivalents thereof.

I claim:

1. An applicator for use with an incontinence device, aid applicator comprising:
an elongated handle; and
a head configured to conform to the shape of an external anal area of a patient and attached to said handle, said head being adapted to fit within an incontinence device including a thin walled bag extending to an opening in an upper end thereof surrounded by an area adapted to attach adhesively to external tissue surrounding an anal sphincter of said patient for bringing an attachment area of said device to bear against said external tissue for adhesive attachment thereto, said head including:
an oval, ring-shaped bearing surface for bearing against said external tissue;
means for adjusting the size of said bearing surface such that said incontinence device may be adapted for use on patients displaying a wide range of anatomical variation, said means including a plurality of concentric rings, each of said plurality of rings having a tubular stem and a lip projecting radially outward from an end of said stem, said concentric rings being disposed in nesting fashion such that the lip of the innermost of said concentric rings is supported by the lip of a ring radially adjacent said innermost ring so that at least said innermost ring may be removed from said applicator head.

2. The applicator of claim 1 wherein the lip of each of said plurality of rings further comprises an upper surface, a conically tapering application surface depending from said upper surface, and a flat bottom surface depending from said tapering application surface such that when said plurality of concentric rings are stacked in nesting arrangement, the bottom surface of the lip of each ring is supported by the upper surface of the lip of a radially outwardly adjacent ring, the tapering application surface of the innermost of said concentric rings forming the bearing surface for application of the device to the patient.

3. The device of claim 1 wherein the applicator head is configured to be generally saddle shaped.

4. The device of claim 1 wherein said at least one of said plurality of concentric rings is configured to be snap fittable inside said adjacent ring for easy removal therefrom.

5. The device of claim 1 wherein at least the head of said applicator is formed of a soft, deformable, smooth surfaced material.

6. The combination of claim 1 wherein the incontinence device is adapted for use upon an anal sphincter of said patient and is formed of a material having an elongation sufficient to expand said bag along a longitudinal axis in response to bowel pressure exerted by said patient and to receive excreta expelled by said patient without obstructing normal bowel movement.

7. The applicator of claim 1 wherein the incontinence device is adapted for use as a fecal incontinence device and is formed of a material having an elongation sufficient to enable said attachment surface to expand and contract in response to changes in a diameter of an anal sphincter of said patient so as not to obstruct normal bowel movement.

* * * * *